(12) United States Patent
Tong et al.

(10) Patent No.: US 10,201,343 B2
(45) Date of Patent: Feb. 12, 2019

(54) SYSTEM FOR DELIVERING AN ANCHOR

(71) Applicant: NeoTract, Inc., Pleasanton, CA (US)

(72) Inventors: Ling-Kang Tong, Fremont, CA (US);
Theodore M Bender, San Anselmo, CA (US); Robert M George, San Jose, CA (US); Joseph Catanese, III, San Leandro, CA (US); Imraan Aziz, Oakland, CA (US)

(73) Assignee: NeoTract, Inc., Pleasanton, CA (US)

( * ) Notice: Subject to any disclaimer, the term of this patent is extended or adjusted under 35 U.S.C. 154(b) by 328 days.

(21) Appl. No.: 14/269,059

(22) Filed: May 2, 2014

(65) Prior Publication Data
US 2014/0330290 A1    Nov. 6, 2014

Related U.S. Application Data

(60) Provisional application No. 61/819,507, filed on May 3, 2013.

(51) Int. Cl.
A61B 17/04    (2006.01)
A61B 17/00    (2006.01)
A61B 17/06    (2006.01)

(52) U.S. Cl.
CPC ...... *A61B 17/0401* (2013.01); *A61B 17/0482* (2013.01); *A61B 2017/00424* (2013.01); *A61B 2017/0409* (2013.01); *A61B 2017/0419* (2013.01); *A61B 2017/06052* (2013.01)

(58) Field of Classification Search
CPC ...... A61B 17/0401; A61B 2017/00424; A61B 2017/0419; A61B 17/0482; A61B 2017/0409; A61B 2017/06052
See application file for complete search history.

(56) References Cited

U.S. PATENT DOCUMENTS

| | | | | |
|---|---|---|---|---|
| 3,643,851 A * | 2/1972 | Green | ............... | A61B 17/0684 227/120 |
| 3,675,688 A * | 7/1972 | Bryan | .................. | A61B 17/128 140/93 D |
| 4,508,253 A * | 4/1985 | Green | .................. | A61B 17/072 227/120 |
| 5,437,680 A * | 8/1995 | Yoon | .................. | A61B 17/0057 606/139 |
| 5,443,197 A * | 8/1995 | Malis | ................. | A61B 17/0682 227/176.1 |
| 2005/0222588 A1 * | 10/2005 | Vandenbroek | ..... | A61B 17/1222 606/142 |
| 2005/0256529 A1 * | 11/2005 | Yawata | ................ | A61B 17/068 606/143 |
| 2009/0099577 A1 * | 4/2009 | Gonzales | ............. | A61B 17/064 606/143 |
| 2010/0023022 A1 * | 1/2010 | Zeiner | ................ | A61B 17/0401 606/139 |
| 2010/0023024 A1 * | 1/2010 | Zeiner | ................ | A61B 17/0401 606/144 |
| 2010/0213241 A1 * | 8/2010 | Bedi | ................ | A61B 17/07207 227/180.1 |
| 2011/0087276 A1 * | 4/2011 | Bedi | .................. | A61B 17/0644 606/219 |

* cited by examiner

*Primary Examiner* — Jing Ou

(57) ABSTRACT

A system for treating a prostate includes a cartridge, a handle configured to receive the cartridge, and an anchor assembly. The cartridge includes the anchor assembly and the handle includes an actuator and a spring mechanism loaded with mechanical energy. The cartridge and handle mate via pivoting and are aligned via alignment features.

12 Claims, 22 Drawing Sheets

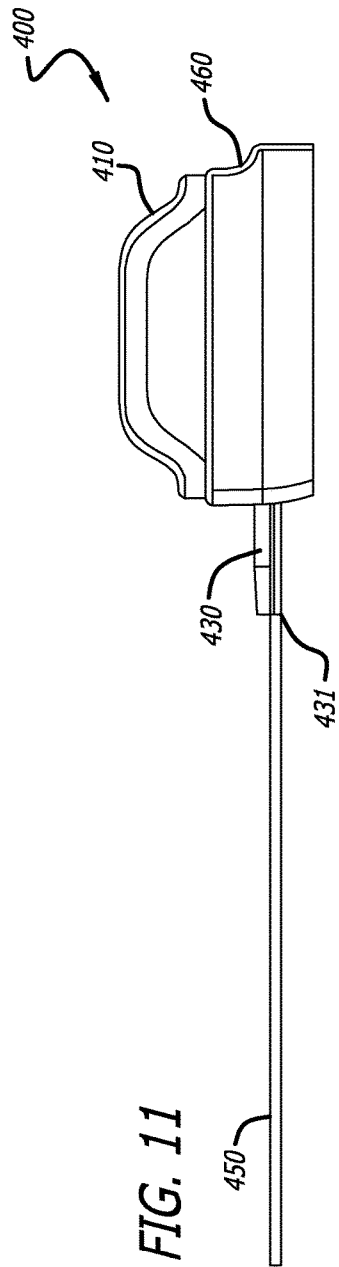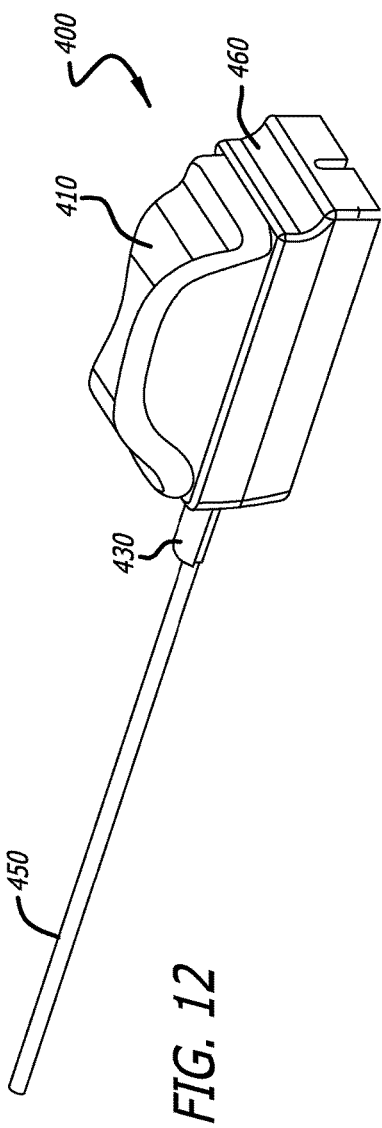

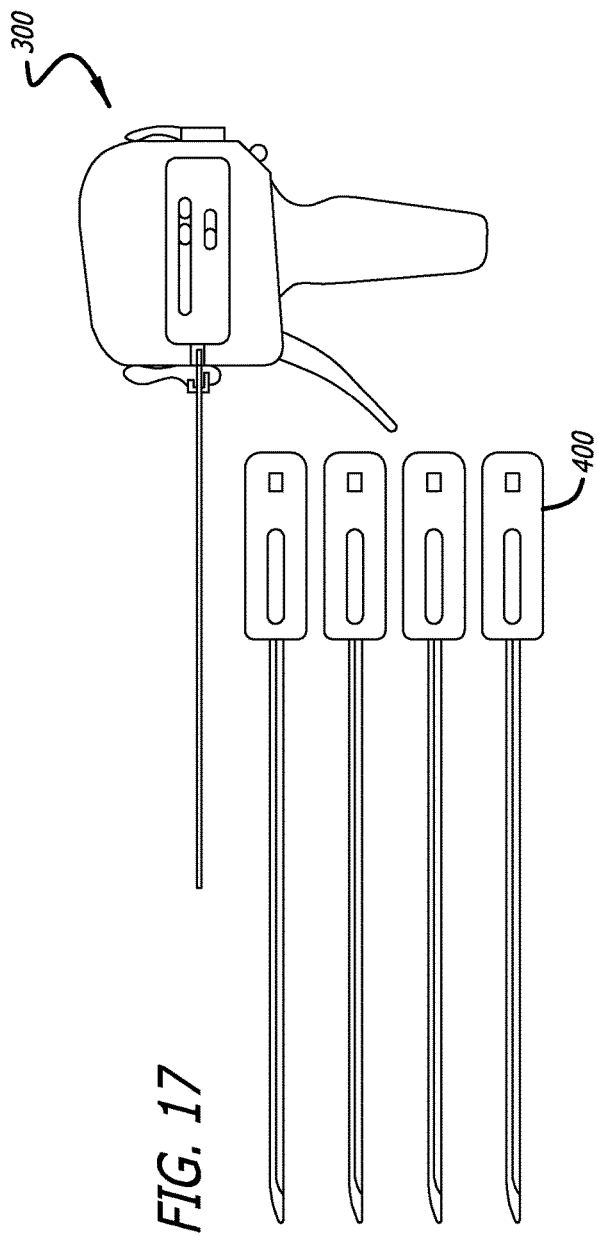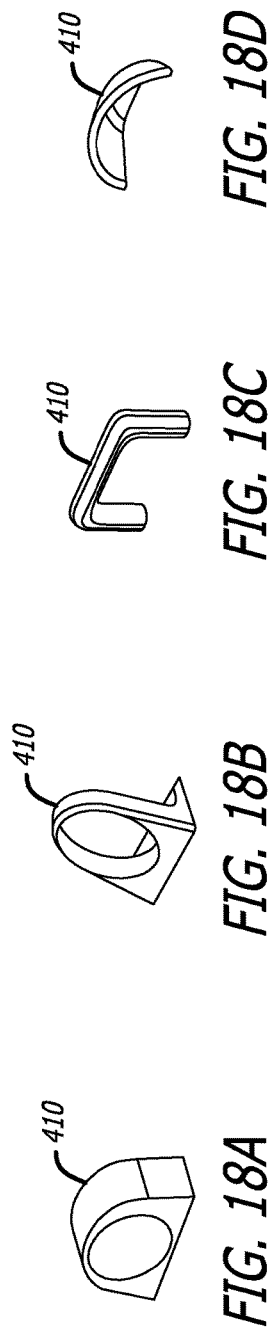
FIG. 17
FIG. 18A
FIG. 18B
FIG. 18C
FIG. 18D

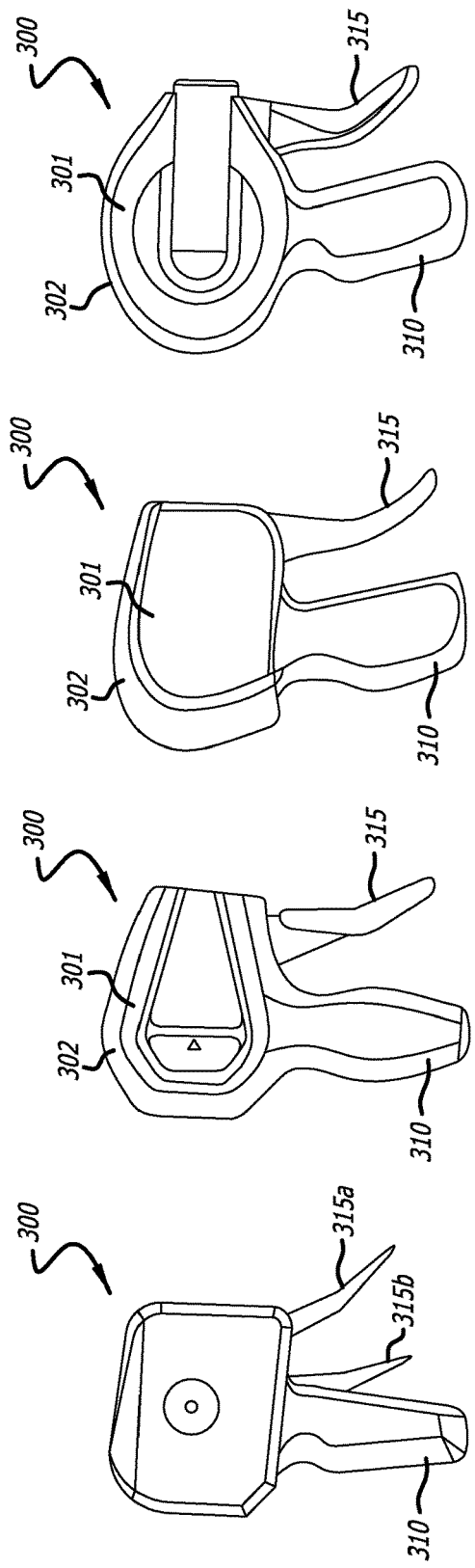

SYSTEM FOR DELIVERING AN ANCHOR

CROSS-REFERENCE TO RELATED APPLICATIONS

This application claims priority to and the benefit of U.S. Provisional Application No. 61/819,507 filed May 3, 2013 entitled "Suture Anchoring Devices and Methods for Use," which application is incorporated herein by reference in its entirety.

BACKGROUND OF THE DISCLOSURE

The present disclosure relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner end of the prostate gland to squeeze the urethra. This pressure on the urethra increases resistance to urine flow through the end of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry lower risks of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for lifting and repositioning of tissues. However, further advances are necessary to ensure an ability to access difficult to reach body structure.

There remains a need for the development of new devices and methods that can be used to deploy multiple anchors from a single delivery device to improve the user experience and minimizing patient discomfort. An ability to access anatomy with minimally invasive instruments while viewing the interventional procedure is also desirable. Moreover, various structures ensuring an effective interventional procedure such as implants having structural memory characteristics have been found to be helpful in certain treatment approaches.

The present disclosure addresses these and other needs.

SUMMARY

Briefly and in general terms, the present disclosure is directed towards an apparatus and method for deploying an anchor assembly within a patient's body to accomplish interventional treatments. A delivery device is provided to access the anatomy targeted for the interventional procedure. Some embodiments of the delivery device include mechanisms configured to deploy one or more anchor assemblies using a single handle assembly and multiple cartridge assemblies. Suitable embodiments of such delivery devices and anchor assemblies are described in co-pending U.S. patent application Ser. No. 13/833,299, filed Mar. 15, 2013, the disclosure of which is incorporated by reference herein in its entirety.

The delivery apparatus of the present disclosure includes various subassemblies that are mobilized via an actuator or other manually accessible structure. The operation of the subassemblies is coordinated and synchronized to ensure accurate and precise implantation of an anchor assembly. In one embodiment, the delivery device is embodied in a tissue approximation assembly that is configured to treat BPH.

In one particular aspect, the present invention is directed towards a delivery device that accomplishes the delivery of a first or distal anchor assembly component at a first location within a patient's body and the delivery of a second or proximal anchor assembly component at a second location within the patient. Further, the delivery device can include mechanisms for efficient reloading of anchor assemblies to minimize patient discomfort and enhance ease of use. The device can also accomplish imparting tension during delivery to a connector to hold it while attaching the proximal anchor in situ. The procedure can be viewed employing a scope inserted in the device. The scope can assume various configurations and can be employed with complementary structure assisting in the viewing function. Also, the delivery device can be sized and shaped to be compatible inside a sheath up to 24 F, preferably a 19 F or 20 F sheath or smaller.

The anchor assembly can be configured to accomplish approximating, retracting, lifting, compressing, supporting, remodeling, or repositioning tissue within the body of a human or animal subject. Moreover, the apparatus configured to deploy the anchor assembly as well as the anchor assembly itself are configured to complement and cooperate with body anatomy.

In one aspect, a system for treating a prostate includes a cartridge, a handle configured to receive the cartridge, and a delivery assembly. The cartridge includes a distal anchor, a connector, and a proximal anchor and the handle includes an actuator, a spring mechanism loaded with mechanical energy. The delivery assembly includes a member that mates with the cartridge to transfer the mechanical energy from the spring mechanism to the cartridge and the actuator operates to reload the mechanical energy.

In one aspect, a system for deploying an anchor assembly includes a cartridge carrying the anchor assembly and a handle configured to couple with the cartridge such that mechanical energy loaded in at least one spring mechanism within the handle is transferred to the cartridge to deploy the anchor assembly. The system includes an actuator configured to initiate transfer of the mechanical energy and restore the majority of the mechanical energy to the spring mechanisms.

In one aspect, a method for delivering a plurality of anchor assemblies includes inserting a cartridge into a handle assembly. The handle assembly includes an actuator and a drive mechanism having a first loaded configuration characterized by a total stored energy and an unloaded configuration. The cartridge includes at least one anchor assembly and a penetrating member. At least one anchor assembly and the penetrating member are configured to advance from a distal portion of the cartridge. The method includes positioning the distal portion of the cartridge at an interventional site adjacent a prostate and operating the actuator to cycle the drive mechanism from the loaded configuration to the unloaded configuration to a second loaded configuration characterized by a total stored energy. Operating the actuator simultaneously delivers at least one anchor assembly to the prostate by transferring load from the drive mechanism to the cartridge. The method includes removing the cartridge.

Various alternative methods of use are contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has myriad other potential surgical, therapeutic, cosmetic or reconstructive applications, such as where a tissue, organ, graft or other material requires approximately, retracting, lifting, repositioning, compression or support.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIGS. 11 and 12 are views of a cartridge of an anchor delivery system.

FIG. 17 depicts a kit including a handle assembly and four cartridge assemblies.

FIGS. 18A through 18D depict various designs for cartridge handles.

FIGS. 20A through 20D depict different shapes and configurations for a handle assembly.

DETAILED DESCRIPTION OF THE PREFERRED EMBODIMENTS

Turning now to the figures, which are provided by way of example and not limitation, the present disclosure is directed to a device configured to deliver multiple anchor assemblies within a patient's body for treatment purposes. The disclosed apparatus can be employed for various medical purposes including but not limited to retracting, lifting, compressing, approximating, supporting, remodeling, or repositioning tissues, organs, anatomical structures, grafts or other material found within a patient's body. Such tissue manipulation is intended to facilitate the treatment of diseases or disorders such as the displacement, compression and/or retraction of the body tissue.

In an aspect of the present disclosure, the delivery device includes a handle assembly supporting an elongate member. The elongate member defines a low profile that is suited to navigate body anatomy to reach an interventional site. Substructure is provided to maintain a longitudinal profile of the elongate member so that the interventional procedure can progress as intended.

In another aspect, one portion of an anchor assembly or implant is positioned and implanted against a first section of anatomy. A second portion of the anchor assembly or implant is then positioned and implanted adjacent to a second section of anatomy for the purpose of retracting, lifting, compressing, approximating, supporting, remodeling, or repositioning the second section of anatomy with respect to the first section of anatomy as well as for the purpose of retracting, lifting, compressing, approximating, supporting, remodeling, or repositioning the first section of anatomy with respect to the second section of anatomy. It is also to be recognized that both a first and second portion of the anchor assembly can be configured to accomplish the desired retracting, lifting, compressing, approximating, supporting, remodeling, or repositioning of anatomy due to tension supplied during delivery via a connector assembly affixed to the first and second portions of the anchor assembly or implant. The delivery device can include an endoscope providing the ability to view the interventional procedure.

Figure 1A:
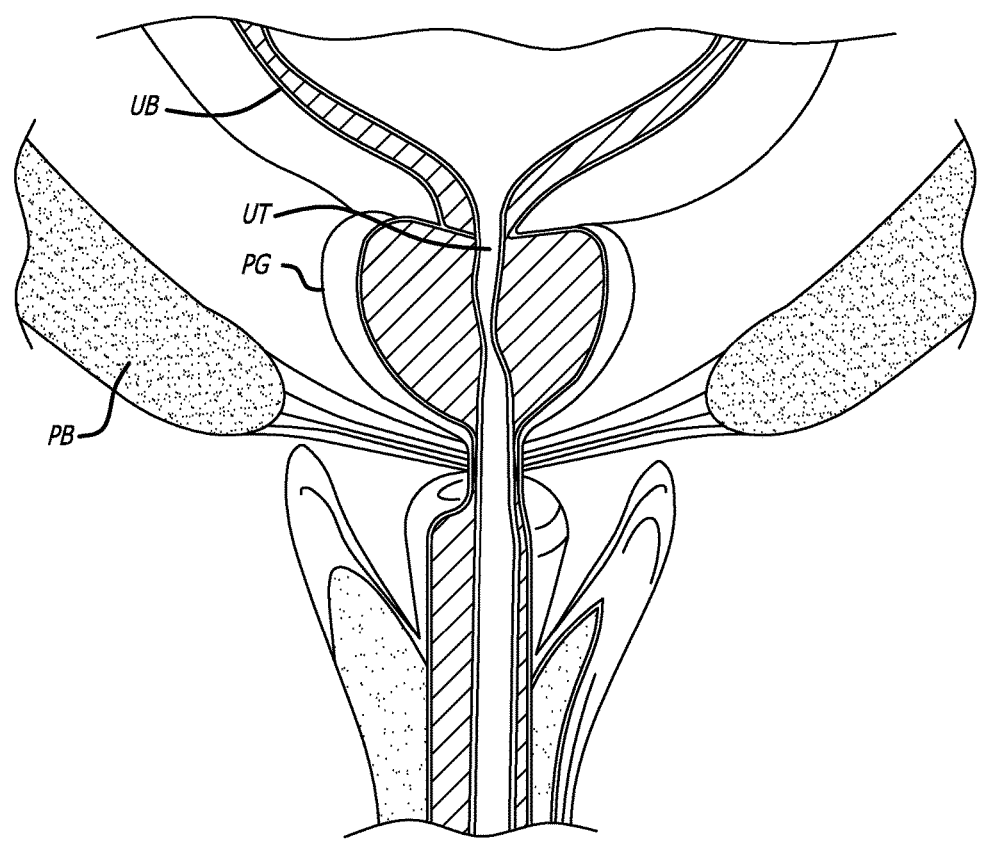
FIG. 1A shows a coronal section through the lower abdomen of a male human suffering from BPH showing a hypertrophied prostate gland.

FIG. 1A shows a coronal section (i.e., a section cut approximately in the plane of the coronal suture or parallel to it) through the lower abdomen of a male human suffering from BPH showing a hypertrophied prostate gland. As depicted in FIG. 1A, the urinary bladder UB is a hollow muscular organ that temporarily stores urine. It is situated behind the pubic bone PB. The lower region of the urinary bladder has a narrow muscular opening called the bladder neck, which opens into a soft, flexible, tubular organ called the urethra UT. The muscles around the bladder neck are called the internal urethral sphincter. The internal urethral sphincter is normally contracted to prevent urine leakage. The urinary bladder gradually fills with urine until full capacity is reached, at which point the sphincters relax. This causes the bladder neck to open, thereby releasing the urine stored in the urinary bladder into the urethra. The urethra conducts urine from the urinary bladder to the exterior of the body. The urethra begins at the bladder neck and terminates at the end of the penis. The prostate gland PG is located around the urethra at the union of the urethra and the urinary bladder. In FIG. 1A, the prostate gland is hypertrophied (enlarged). This causes the prostate gland to press on a region of the urethra. This in turn creates an undesired obstruction to the flow of urine through the urethra.

Figure 1B:
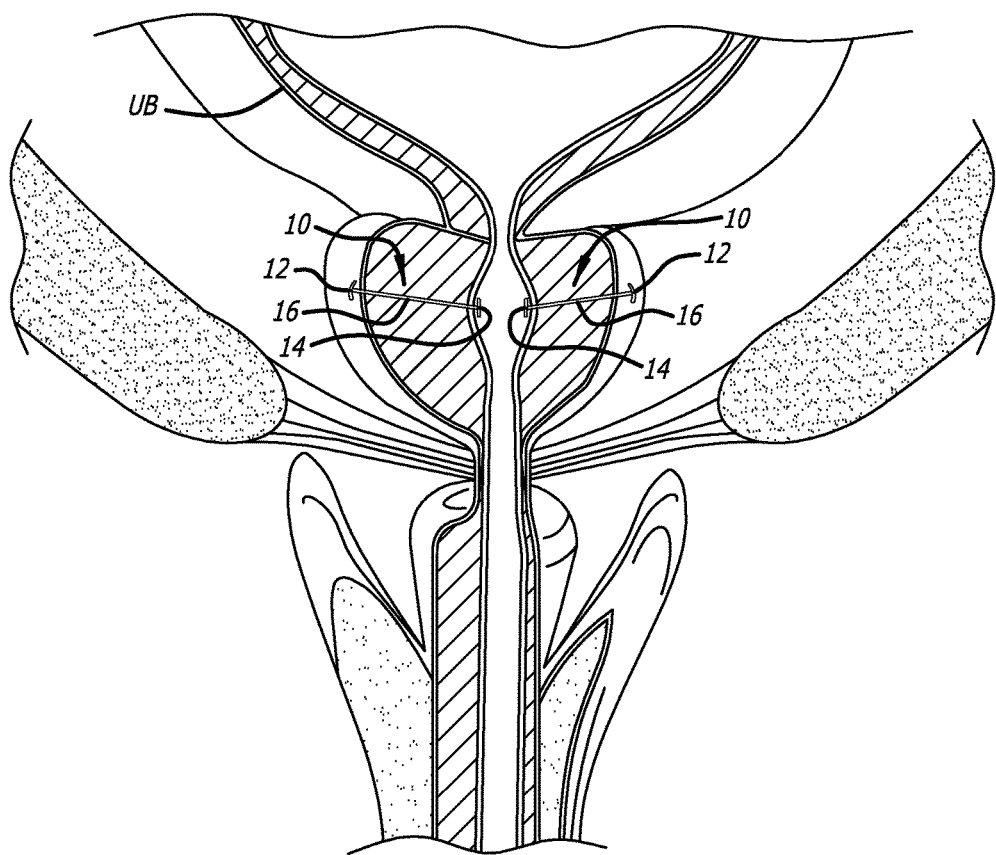
FIG. 1B shows a coronal section through the lower abdomen of a male human suffering from BPH showing a hypertrophied prostate gland treated with an embodiment of the device of the present invention.

FIG. 1B shows a coronal section through the lower abdomen of a male human suffering from BPH showing a hypertrophied prostate gland treated with an embodiment of the device of the present invention. It has been discovered that the enlarged prostate gland is compressible and can be retracted so as to relieve the pressure from the urethra. In accordance with one embodiment of the present invention, a retaining device can be placed through the prostate gland in order to relieve the pressure on the urethra. In FIG. 1B, a retainer 10 is implanted in the prostate gland. Retainer 10 comprises a distal anchor 12 and a proximal anchor 14. Distal anchor 12 and a proximal anchor 14 are connected by a connector 16. The radial distance from the urethra to distal anchor 12 is greater than the radial distance from the urethra to proximal anchor 14. The distance or tension between the anchors is sufficient to compress, displace or change the orientation of an anatomical region between distal anchor 12 and proximal anchor 14. The connector 16 can be inelastic so as to maintain a constant force or distance between the proximal and distal anchors or be elastic so as to attempt to draw the proximal and distal anchors closer together. In the embodiment shown in FIG. 1B, distal anchor 12 is located on the outer surface of the capsule of prostate gland CP and acts as a capsular anchor. Alternatively, distal anchor 12 may be embedded inside the tissue of prostate gland PG or in the surrounding structures around the prostate such as periosteum of the pelvic bones, within the bones themselves, pelvic fascia, coopers ligament, muscles traversing the pelvis or bladder wall. Also, in the embodiment shown in FIG. 1B, proximal anchor 14 is located on the inner wall of urethra UT and acts as a urethral anchor. Alternatively, proximal anchor 14 may be embedded inside the tissue of prostate gland PG or surrounding structures as outlined above. Distal anchor 12 and proximal anchor 14 are implanted in the anatomy such that a desired distance or tension is created in connector 16. This causes distal anchor 12 and proximal anchor 14 to retract or compress a region of prostate gland PG to relieve the obstruction shown in FIG. 1A. In FIG. 1B, two retainers 10 are implanted in prostate gland PG. Each retainer 10 is implanted in a lateral lobe (side lobe) of prostate gland PG. The various methods and devices disclosed herein may be used to treat a single lobe or multiple lobes of the prostate gland or other anatomical structures. Similarly, two or more devices disclosed herein may be used to treat a single anatomical structure. For example, a lateral lobe of prostate gland PG may be treated using two retainers 10. One or more retainers may be deployed at particular angles to the axis of the urethra to target one or more lateral lobes and/or middle lobe of the prostate gland. In one embodiment, retainer 10 is deployed between the 1 o'clock and 3 o'clock position relative to the axis of the urethra to target the left lateral lobe of the prostate gland. In another embodiment, retainer 10 is deployed between the 9 o'clock and 11 o'clock position relative to the axis of the urethra to target the right lateral lobe of the prostate gland. In another embodiment, retainer 10 is deployed between the 4 o'clock and 8 o'clock position relative to the axis of the urethra to target the middle lobe of the prostate gland.

Figure 1C:
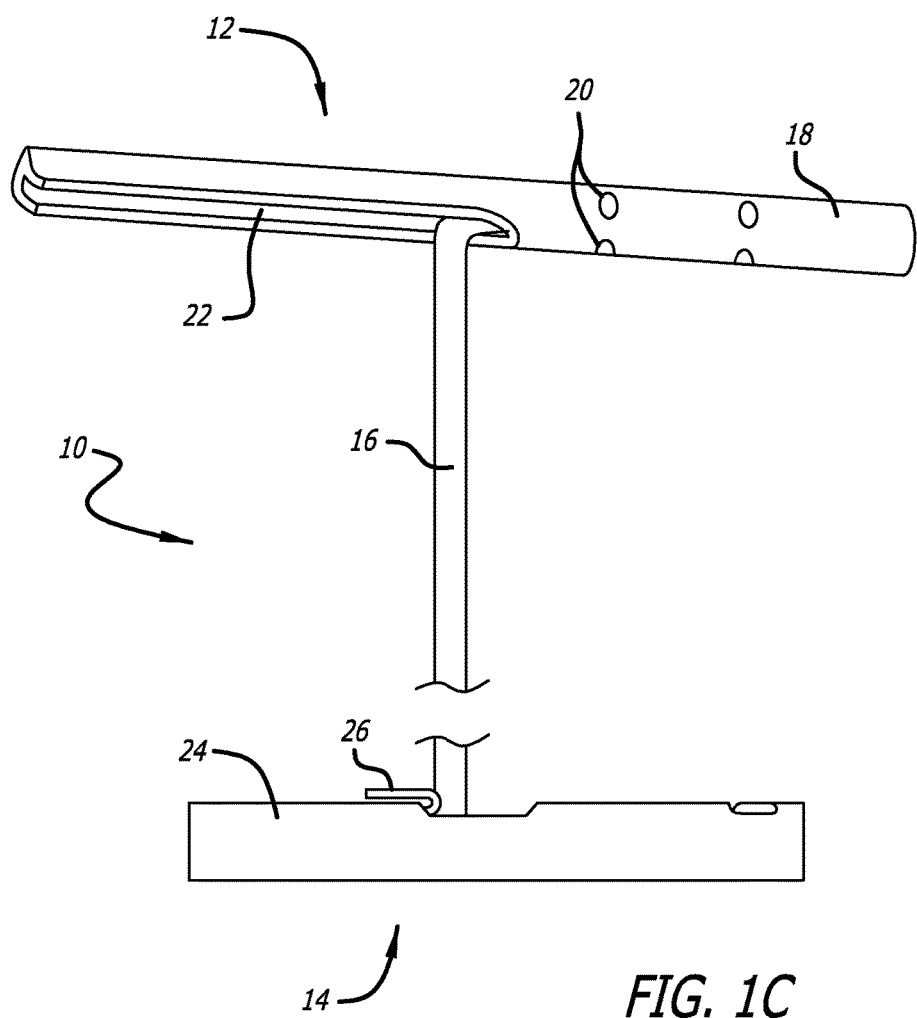
FIG. 1C shows a side view of an embodiment of the retainer shown in FIG. 1B.
Figure 1D:
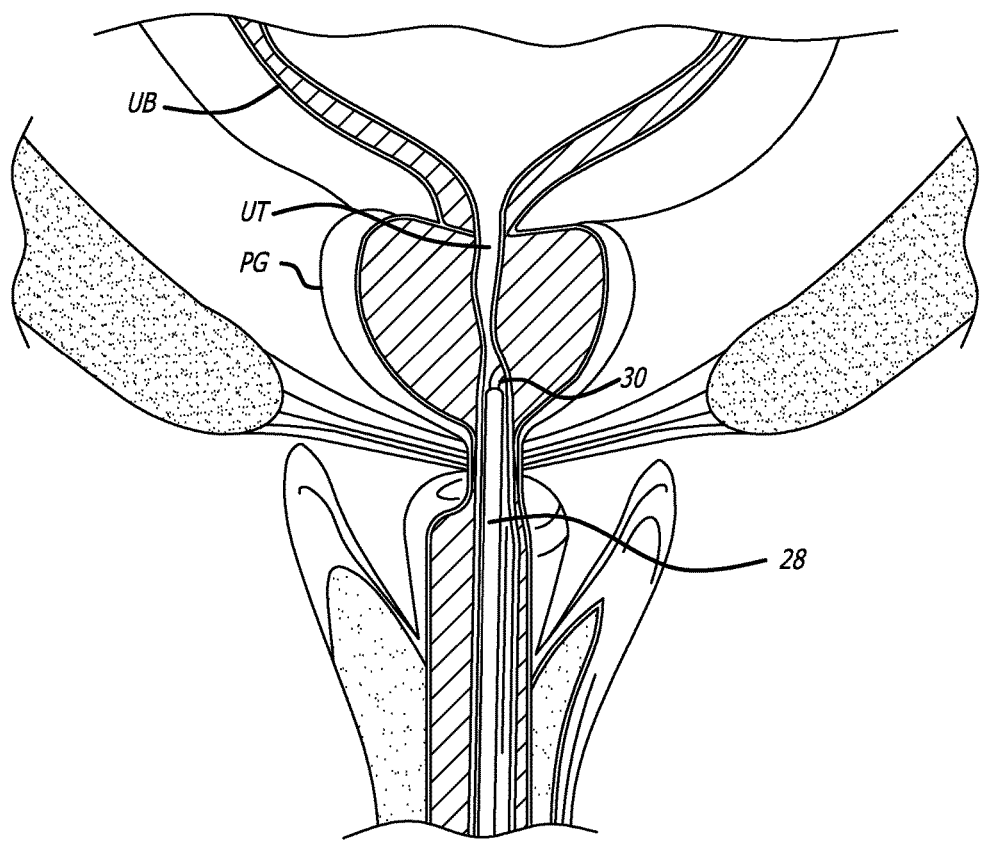
FIGS. 1D through 1J show the various steps of a method of treating a prostate gland by the retainer shown in FIG. 1C.

FIG. 1C shows a side view of one embodiment of the retainer shown in FIG. 1B. FIG. 1C shows retainer 10 comprising distal anchor 12 and proximal anchor 14. Distal anchor 12 and proximal anchor 14 are connected by connector 16. In the embodiment shown in FIG. 1C, distal anchor 12 comprises a tube 18 having a lumen. Tube 18 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, EPTFE, shape memory polymers, such as polyesterurethane, polyetherurethane, polyetherpolyesters, polyetherpolyamines or combinations of oligo e-caprolactore diol and oligo p-dioxanone diol polymers, etc. Connector 16 is attached to tube 18. In one embodiment, connector 16 is a USP size 0 polypropylene monofilament suture. In the embodiment shown in FIG. 1C, a distal region of connector 16 is located in the lumen of tube 18 such that the distal tip of connector 16 emerges out of one end of the lumen of tube 18. The distal tip of connector 16 is enlarged, such that the diameter of the enlarged distal tip of connector 16 is greater than the inner diameter of tube 18. In one embodiment, the diameter of connector 16 is 0.014 inches and the diameter of the enlarged distal tip of connector 16 is 0.025 inches. In one embodiment, the enlarged distal tip of connector 16 is created by controlled melting of the distal tip of connector 16. This attaches connector 16 to tube 18. Tube 18 may comprise one or more additional attachment mechanisms to attach a distal region of connector 16 to tube 18. In one embodiment, the distal region of connector 16 is attached to tube 18 by a suitable biocompatible adhesive. In the embodiment shown in FIG. 1C, the distal region of connector 16 is attached to tube 18 by one or more inwardly opening flaps 20 that are cut in the material of tube 18. Flaps 20 grip connector 16 and thus prevent the relative motion of connector 16 and tube 18. The angle between one of flaps 20 and connector 16 may range from 1 degree to 90 degrees. Tube 18 further comprises a longitudinal slot 22. Longitudinal slot 22 extends from one end to roughly the mid section of tube 18. Connector 16 emerges out of this longitudinal slot 22. Thus, when connector 16 is pulled in the proximal direction, distal anchor 12 assumes a T-shape that helps to anchor distal anchor 12 to an anatomical structure. Distal anchor 12 may comprise a sharp edge to help penetrate distal anchor 12 through the anatomy. In a preferred embodiment, distal anchor 12 is constructed by laser cutting and electropolishing a nickel-titanium alloy (e.g., nitinol) tube made of 50.8% nickel-49.2% titanium. In the preferred embodiment, the outer diameter of tube 18 is 0.026 inches, the inner diameter of tube 18 is 0.015 inches, the length of tube 18 is 0.315 inches and the length of longitudinal slot 22 is 0.170 inches.

In the embodiment shown in FIG. 1C, proximal anchor 14 comprises a tube 24 comprising a lumen. Tube 24 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, ePTFE, such as polyesterurethane, polyetherurethane, polyetherpolyesters, polyetherpolyamines or combinations of oligo e-caprolactone diol and oligo p-dioxanone diol polymers, etc. An outwardly opening flap 26 is cut through the material of tube 24. Flap 26 is folded on the outer surface of tube 18 as shown in FIG. 1C. This creates an opening to the lumen of tube 24 that is lined by the atraumatic edge of the folded flap 26. Connector 16 enters tube 24 through this opening to the lumen of tube 24. Proximal anchor 14 further comprises an attachment mechanism to attach connector 16 to tube 24. Connector 16 can be made of suitable elastic or non-elastic materials including, but not limited to metals, polymers, etc. Other proximal anchor and distal anchor concepts are within the scope of the invention, such as v-shaped proximal anchors that are press fit onto a connector. Typical examples of such materials include, but are not limited to stainless steel 304, stainless steel 316, nickel-Titanium alloys, suture materials, titanium, silicone, nylon, polyamide, polyglycolic acid, polypropylene, Pebax, PTFE, ePTFE, silk, gut, or any other braided or mono-filament material. In a preferred embodiment, tube 24 has a length of 0.236 inches and an outer diameter of 0.027 inches and an inner diameter of 0.020 inches. The length of opening to the lumen of tube 24 is approximately 0.055 inches. In the preferred embodiment, the attachment mechanism comprises a lock pin that frictionally attaches connector 16 to tube 24. The lock pin and tube 24 are made of stainless steel 316L. In the preferred embodiment, tube 24 is laser cut or stamped and then electropolished. Lock pin is constructed using EDM (electrical discharge machining) and then passivated.

FIGS. 1D through 1J show the various steps of a method of treating a prostate gland by the retainer shown in FIG. 1C. Similar methods may be also used to deploy retainer or compression devices in other anatomical structures. In the step shown in FIG. 1D, a sheath 28 such as a standard resectoscope sheath is introduced into the urethra (transurethrally). Sheath 28 is advanced through urethra UT such that the distal end of sheath 28 is positioned near a region of urethra UT that is obstructed by a hypertrophied prostate gland PG. Distal anchor delivery device 30 is introduced through sheath 28. Distal anchor delivery device 30 can be placed in the sheath 28 after the distal end of sheath 28 is positioned near the region of the urethra UT that is obstructed or the distal anchor delivery device 30 can be pre-loaded in the sheath 28 before positioning of the sheath 28. Distal anchor delivery device 30 is advanced through sheath 28 such that the distal end of distal anchor delivery device 30 emerges out of the distal end of sheath 28. Distal anchor delivery device 30 is oriented such that a working channel opening of distal anchor delivery device 30 points towards a lateral lobe of prostate gland PG.

Figure 1E:
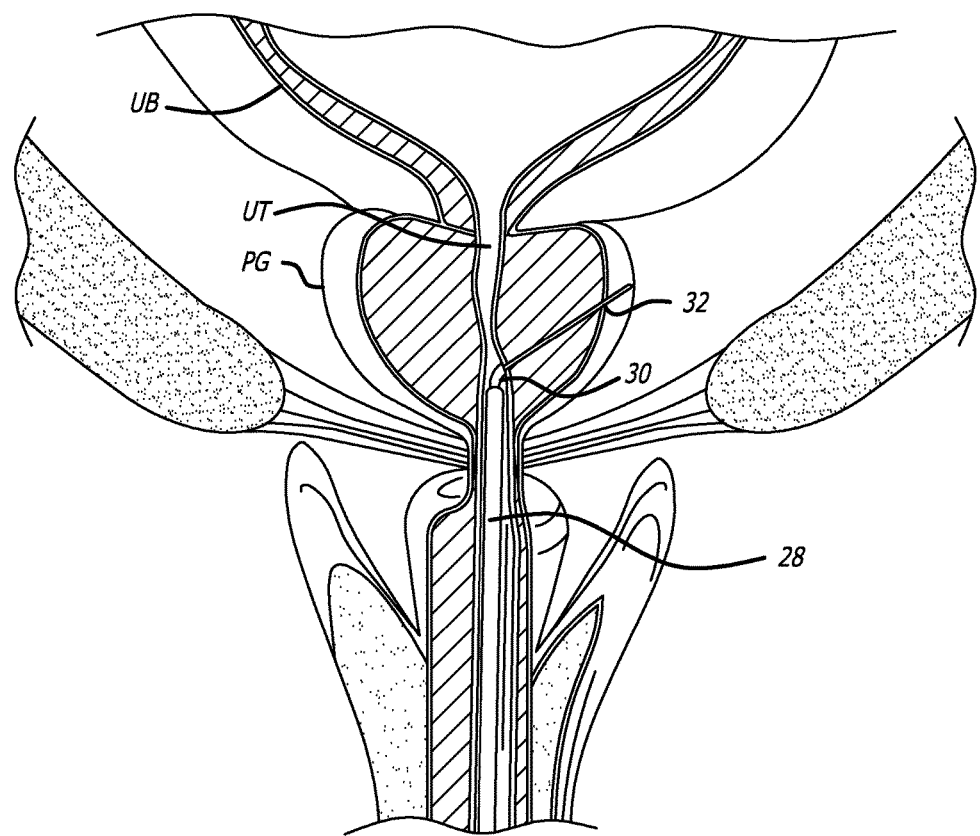

In the step shown in FIG. 1E, a needle 32 is introduced through distal anchor delivery device 30. Needle 32 can be placed in distal anchor delivery device after the distal anchor delivery device 30 is advanced through sheath 28 or the needle 32 can be pre-loaded in the distal anchor delivery device 30. In one embodiment, needle 32 is a 20 gauge needle. Needle 32 is advanced through distal anchor delivery device 30 such that it emerges through the working channel opening. Needle 32 is further advanced such that it penetrates through the tissue of prostate gland PG and the distal end of needle 32 emerges out of the capsule of prostate gland CP.

Figure 1F:
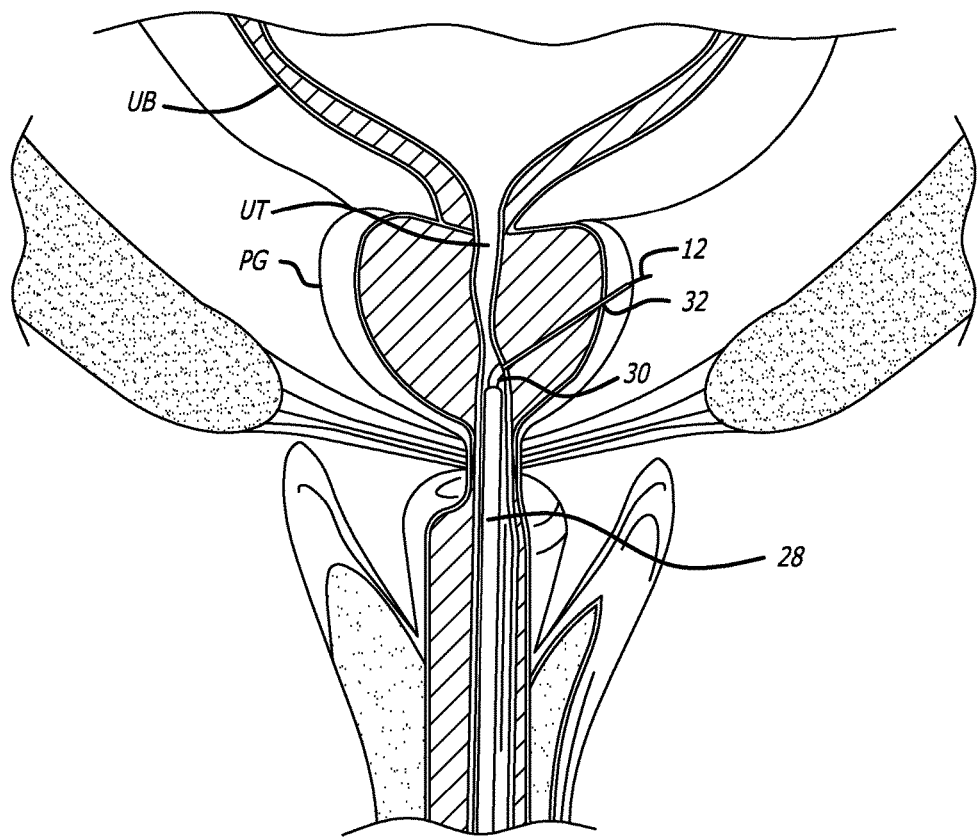

In the step shown in FIG. 1F, distal anchor 12 connected to connector 16 is advanced through needle 32. Distal anchor 12 can be pre-loaded in needle 32 or can be loaded in needle 32 after needle 32 has been advanced through distal anchor delivery device 30. Distal anchor 12 is advanced through needle 32 such that it emerges out of the distal end of needle 32. In alternate embodiments, the distal anchor can be held in place by a pusher or connector while the needle is retracted, thus exposing the distal anchor.

Figure 1G:
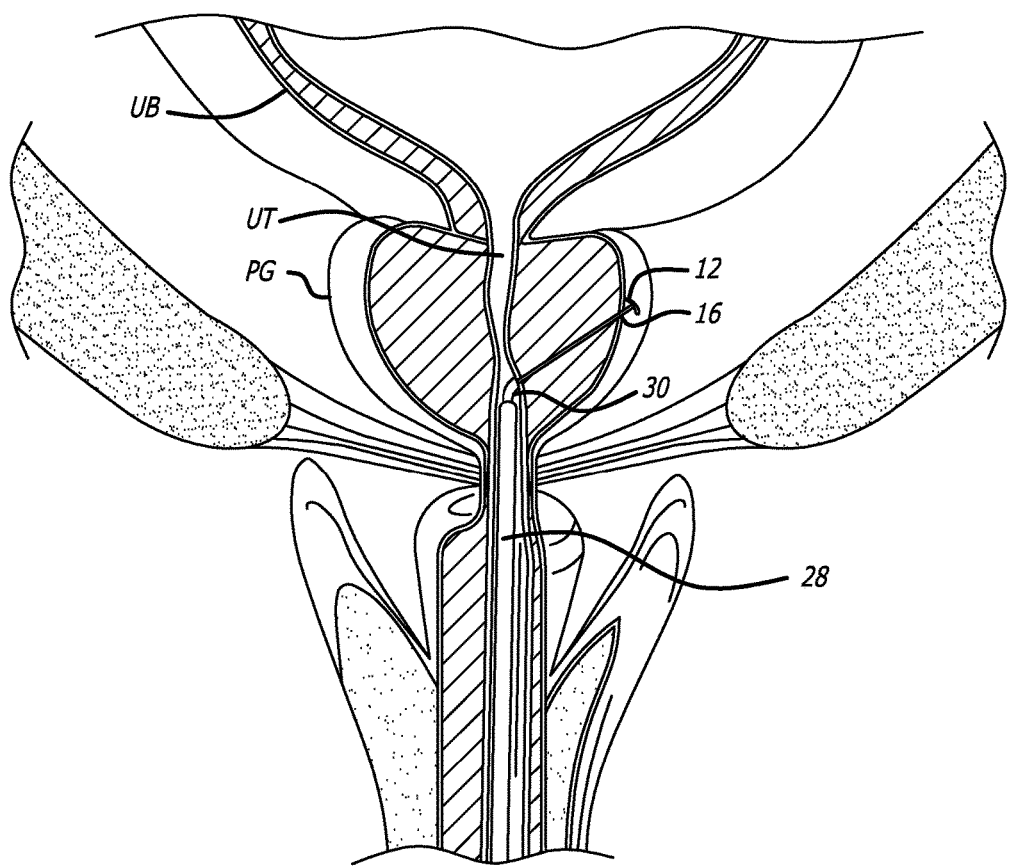

In the step shown in FIG. 1G, needle 32 is removed from distal anchor delivery device 30 by pulling needle 32 in the proximal direction.

Figure 1H:
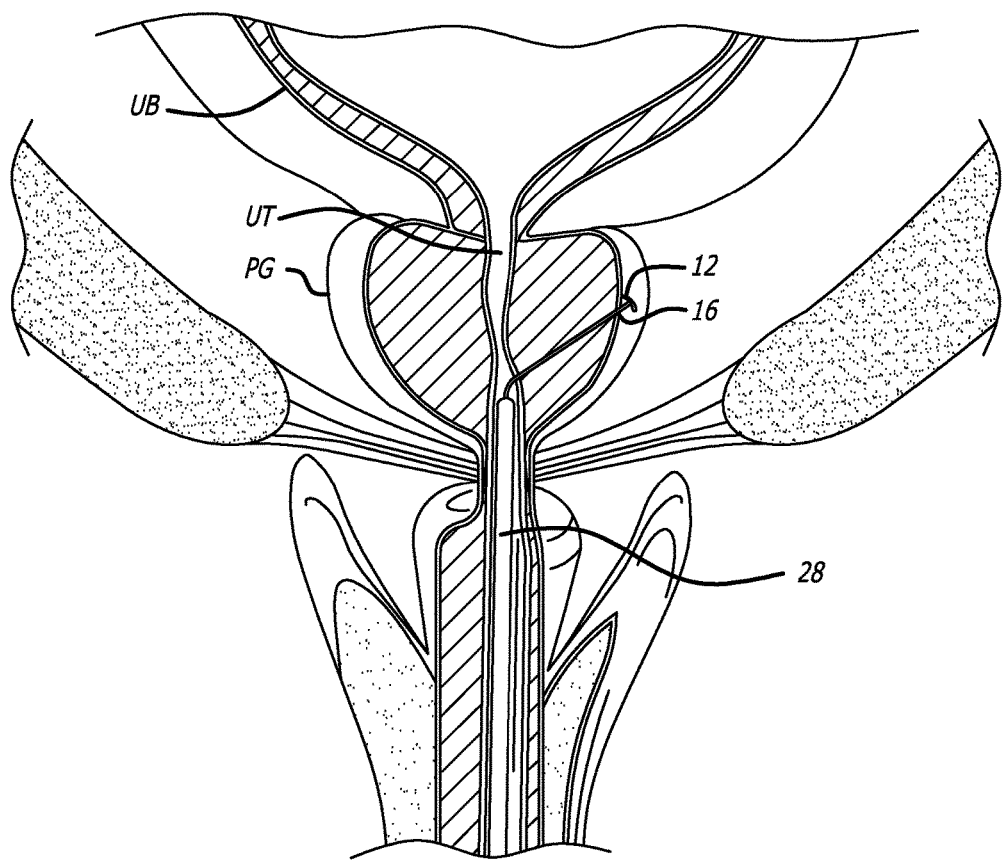

In the step shown in FIG. 1H, distal anchor delivery device 30 is removed from sheath 28 by pulling distal anchor delivery device 30 in the proximal direction. Also, connector 16 is pulled to orient distal anchor 12 perpendicularly to connector 16.

Figure 1I:
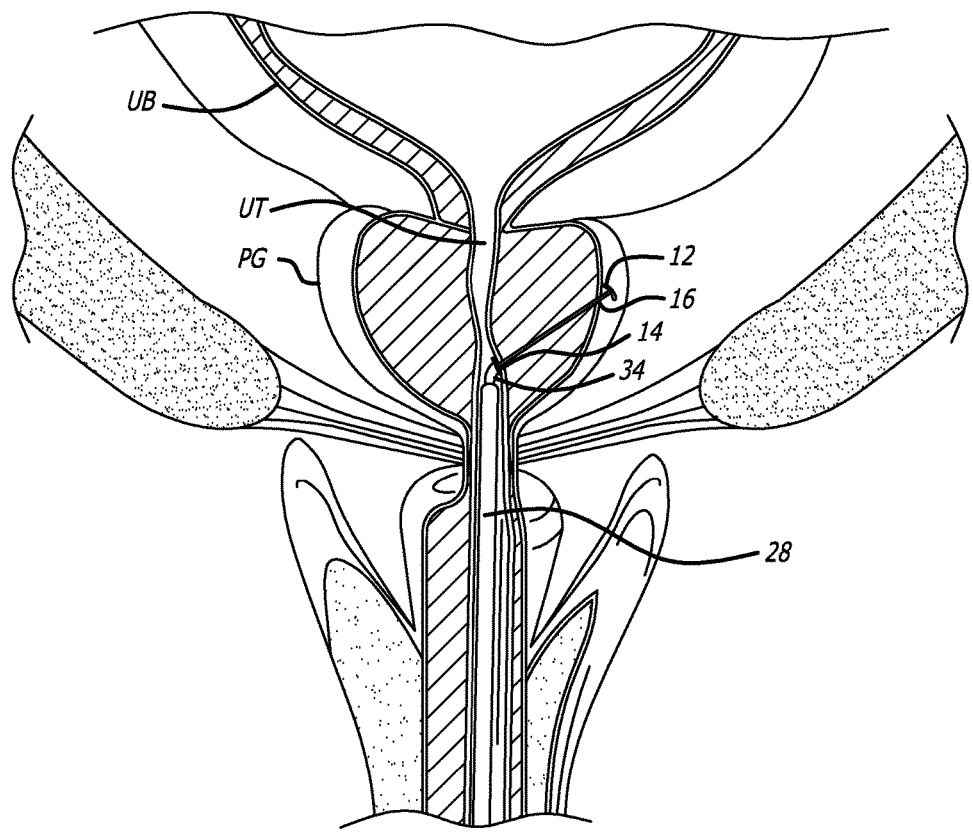

In the step shown in FIG. 1I, connector 16 is passed through proximal anchor 14 located on a proximal anchor delivery device 34. Proximal anchor delivery device 34 is advanced through sheath 28 such that the distal end of proximal anchor delivery device 34 emerges out of the distal end of sheath 28. A desired tension is introduced in connector 16 such that distal anchor 12 is pulled by connector 16 with a desired force. Alternatively, the proximal anchor can be visualized through an endoscope or under fluoroscopy and advanced along the connector until the desired refraction of the tissue is achieved. In other embodiments, the proximal anchor is a v-shaped or clothespin-shaped piece that is forced, in some cases at high speed, onto the connector to fixedly engage the connector.

Figure 1J:
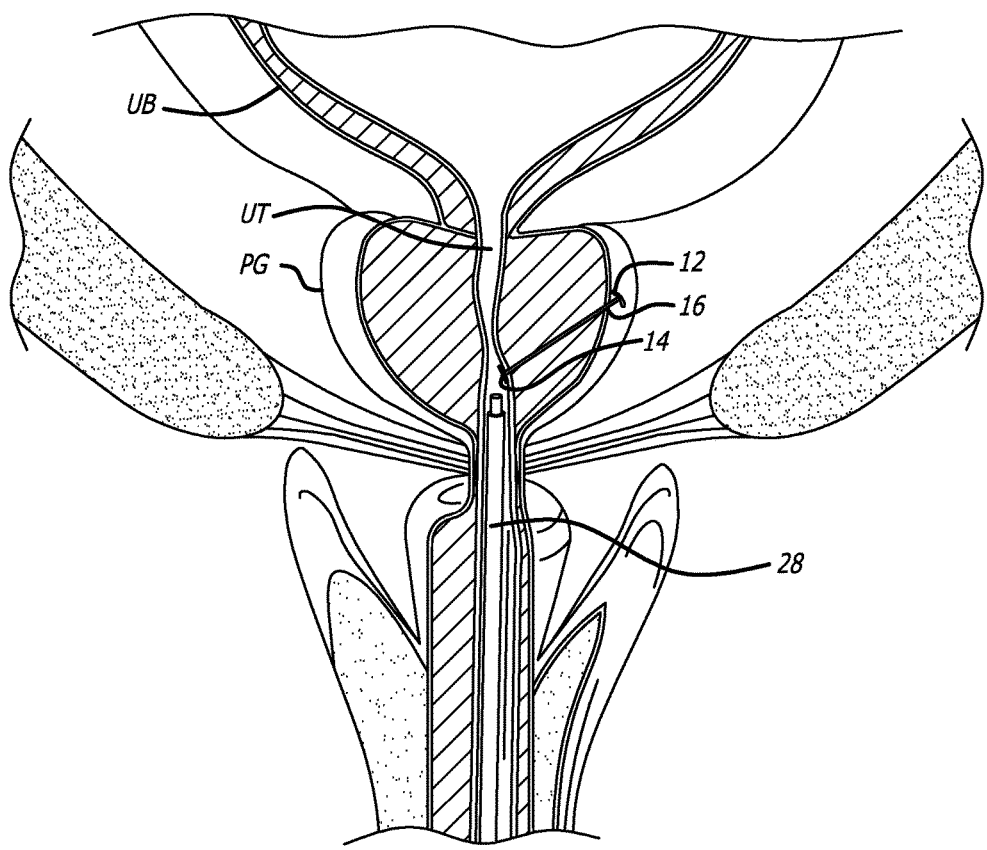

In the step shown in FIG. 1J, connector 16 is attached to proximal anchor 14. Proximal anchor 14 is also released from proximal anchor delivery device 34, thus deploying proximal anchor 14 in the anatomy. Proximal anchor delivery device 34 and sheath 28 are removed form the anatomy. Retainer 10 comprising distal anchor 12, proximal anchor 14 and connector 16 is used to retract, lift, support, reposition or compress a region of prostate gland PG located between distal anchor 12 and proximal anchor 14. This method may be used to retract, lift, support, reposition or compress multiple regions or lobes of the prostate gland PG. In the method shown in FIGS. 1D through 1J, distal anchor 12 is deployed on the outer surface of the capsule of prostate gland CP. Thus, distal anchor 12 acts as a capsular anchor. Alternatively, distal anchor 12 may be deployed inside the tissue of prostate gland PG or beyond the prostate as outlined previously. Similarly, in the method shown in FIGS. 1D through 1J, proximal anchor 14 is deployed on the inner wall of urethra UT and acts as a urethral anchor. Alternatively, proximal anchor 14 may be deployed inside the tissue of prostate gland PG.

The tissue approximation anchor shown in FIG. 1C is designed to be useable in a physician's clinical office environment (in contrast to requiring a hospital environment) with a delivery tool. The delivery tool is used through a 19 F or 20 F sheath in one preferred embodiment. Additionally, the material selection and construction of the tissue approximation anchor still allows for a subsequent TURP procedure to be performed, if necessary, on the prostate. In this suture-based, tissue approximation technique, a needle delivery mechanism is used to implant an anchor assembly.

Figure 2:
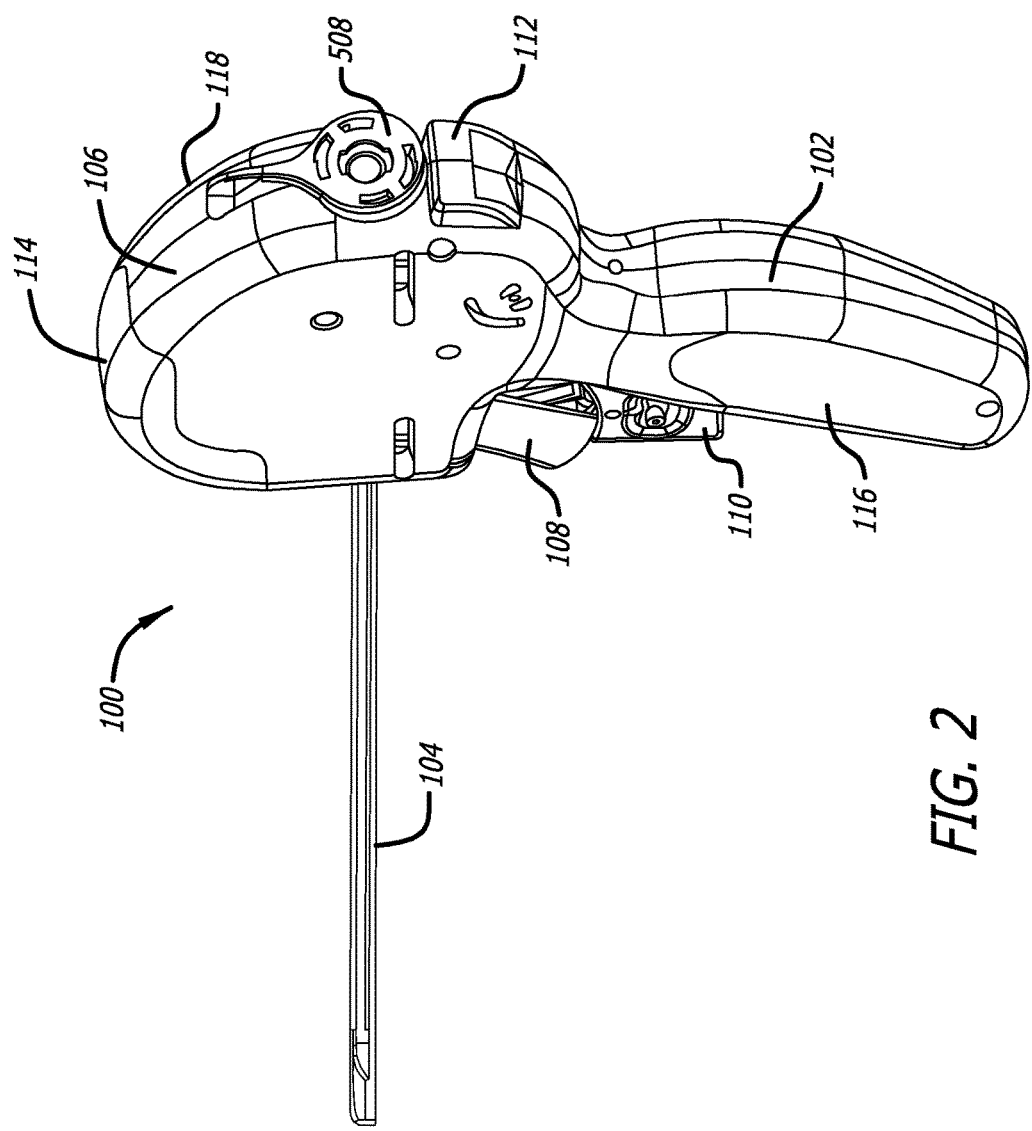
FIG. 2 is a perspective view depicting one embodiment of an anchor delivery system.
Figure 3:
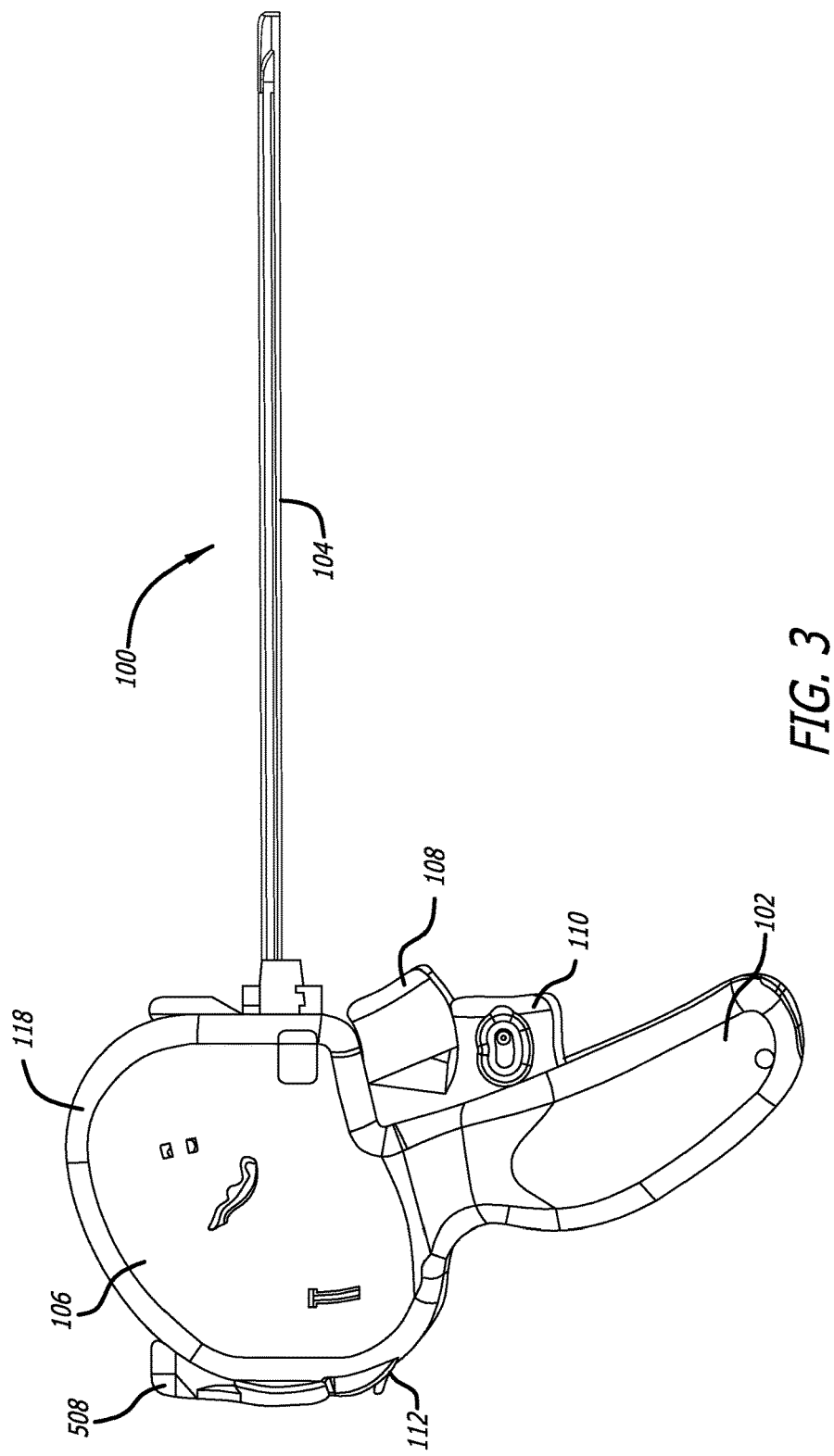
FIG. 3 is a right side view depicting the anchor delivery system of FIG. 2.
Figure 4:
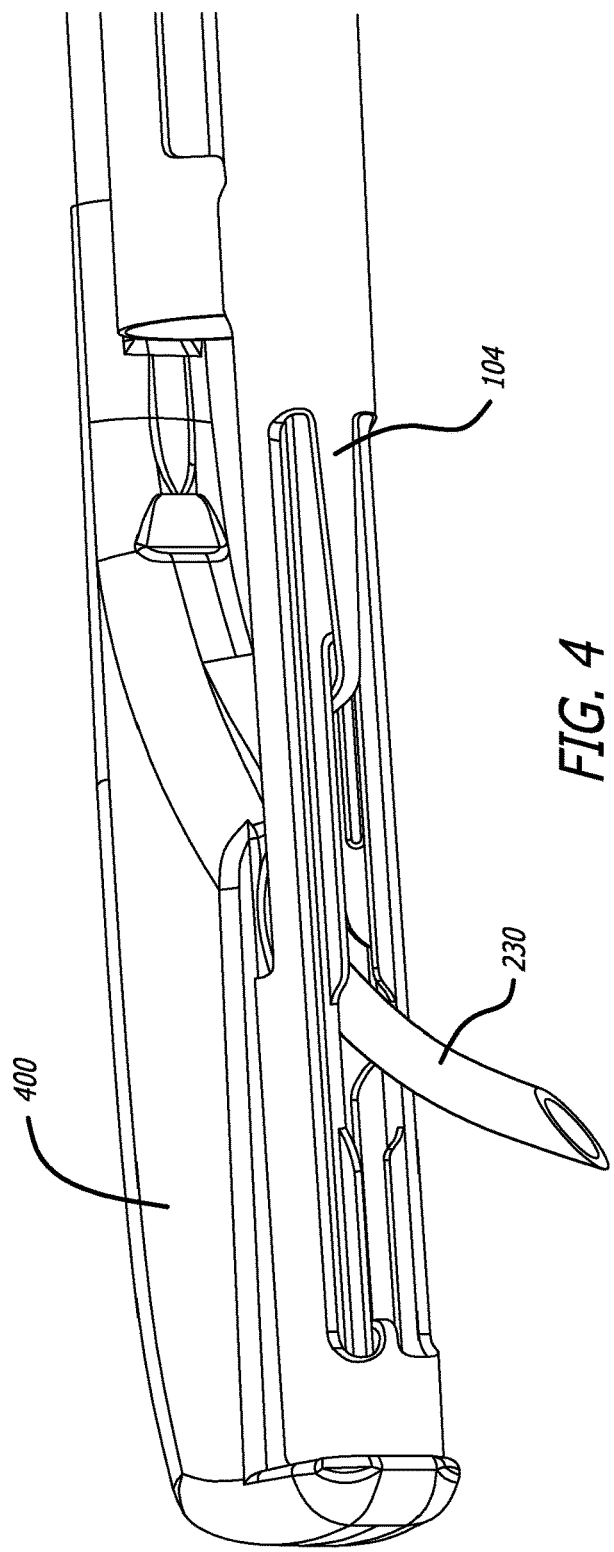
FIG. 4 is a perspective view in partial cross-section depicting partial advancement of a needle assembly.

Referring now to FIGS. 2-4, there is shown one embodiment of a delivery device 100. This device is configured to include structure that is capable of both gaining access to an interventional site as well as assembling and implanting one or more anchor assemblies or implants within a patient's body. The delivery device 100 can be configured to assemble and implant a single anchor assembly or implant a single bodied anchor or multiple anchors or anchor assemblies. The device is further contemplated to be compatible for use with a 19 F or 20 F sheath. The device additionally includes structure configured to receive a conventional remote viewing device (e.g., an endoscope) so that the steps being performed at the interventional site can be observed.

Prior to use of the present device 100, a patient typically undergoes a five day regimen of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to elongate member 104. Elongate member 104 can house components employed to construct an anchor assembly and is sized to fit into a 19 F or 20 F cystosopic sheath for patient tolerance during a procedure in which the patient is awake rather than under general anesthesia. The assembly is intended to include structure to maintain its positioning within anatomy.

The anchor delivery device 100 further includes a number of subassemblies. A handle case assembly 106 including mating handle parts that form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members that facilitate assembly and delivery of an anchor assembly at an interventional site. A needle actuator 108 is provided and as described in detail below, effectuates the advancement of a needle assembly to an interventional site. In one approach, the needle assembly moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle refraction lever assembly 110 is also provided and when actuated causes the needle assembly to be withdrawn and expose the anchor assembly.

In one particular, non-limiting use in treating a prostate, the elongate member 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate member 104 is advanced within the patient until a leading end thereof reaches a prostate gland (PG). In a specific approach, the side(s) (or lobe(s)) of the prostate to be treated is chosen while the device extends through the bladder and the device is turned accordingly. The inside of the prostate gland, including the adenoma, is spongy and compressible and the outer surface, including the capsule, of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

The delivery device is at this stage configured in a ready state. The needle actuator 108 and the needle retracting lever 110 are in an inactivated position.

Upon depression of the needle actuator 108, the needle 230 (See FIG. 4) is advanced from within the elongate member 104. The needle can be configured so that it curves back toward the handle as it is ejected. In use in a prostate intervention, the needle is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (such as wetness) that may degrade effectiveness of needle penetration.

Certain anchor delivery devices include springs as part of the mechanisms that drive a needle or penetrating member, deploy an anchor, cut a connector, or perform other functions related to device delivery. The devices may include springs that are preloaded with potential energy when the user removes the device from packaging. Preloaded springs can be susceptible to degradation over time when stored in a loaded state, whether that state is tension or compression. Spring degradation may affect a device's shelf life. Also, spring degradation can affect the consistency of the device as the spring force can change over time. Further, loaded components may creep due to constant stress.

Figure 5:
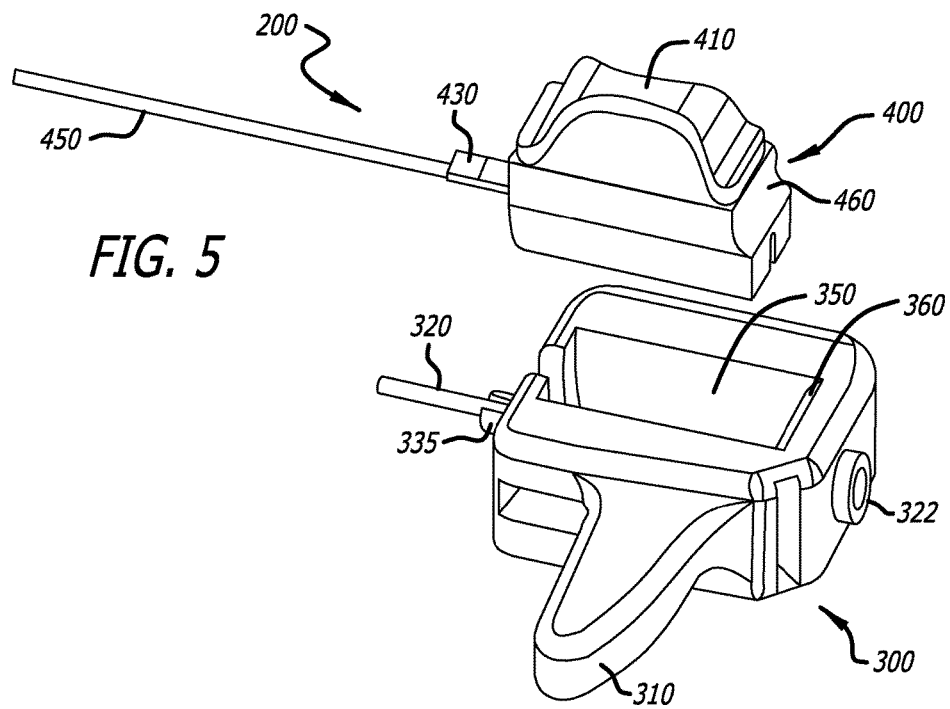
FIG. 5 is a perspective view of an anchor delivery system including a cartridge and a handle.

FIG. 5 illustrates one embodiment of an anchor delivery system 200 including a handle assembly 300 and a cartridge assembly 400. Cartridge assembly 400 is sized, shaped, and configured to couple to handle assembly 300. Cartridge assembly 400 contains one or more anchors, such as retainer 10 depicted in FIG. 1C. Cartridge assembly 400 includes features that mate with features on the handle assembly 300 to transmit mechanical forces from the handle assembly 300 to the cartridge assembly 400. For example, squeezing a lever (not pictured) on handle grip 310 can actuate mechanical forces, such as spring loaded mechanical forces, that are transmitted to the cartridge assembly 400 for deploying an anchor, such as retainer 10.

Handle assembly 300 includes handle shaft 320, which has a lumen configured to allow passage of an endoscope through it. Such an endoscope (not pictured) can extend proximally through the handle assembly 300 and out scope lock 322. Handle assembly 300 includes cartridge chamber 350, which is configured to accept the body portion of cartridge assembly 400. Within cartridge chamber 350 are features that mate with the features of cartridge assembly 400 to transmit mechanical forces.

At the proximal end of the interior of cartridge chamber 350 is guide 360, which protrudes distally from the proximal wall of the cartridge chamber 350. A proximal portion of cartridge assembly 400 includes receiver 460, which interacts with guide 360 when the cartridge assembly 400 is placed within cartridge chamber 350. Cartridge assembly 400 can be held be cartridge grip 410 when being manipulated to be placed within cartridge chamber 350.

Figure 6:
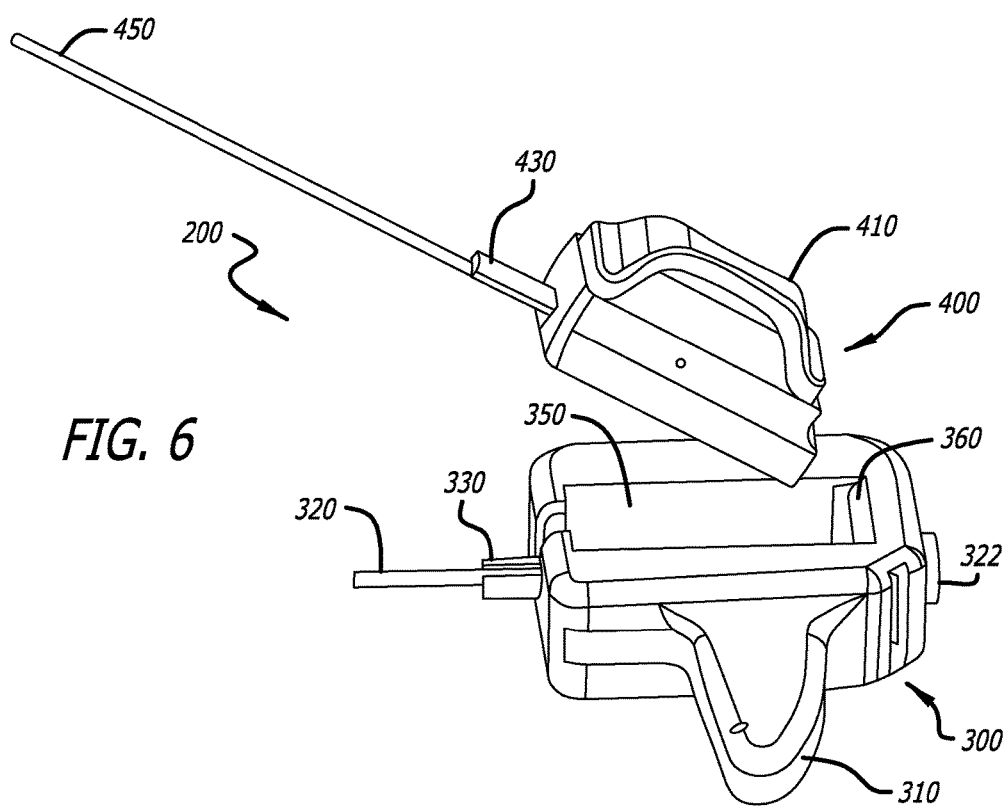
FIGS. 6 through 8 are perspective views of an anchor delivery system including a cartridge and a handle where the cartridge is being positioned within the handle.
Figure 7:
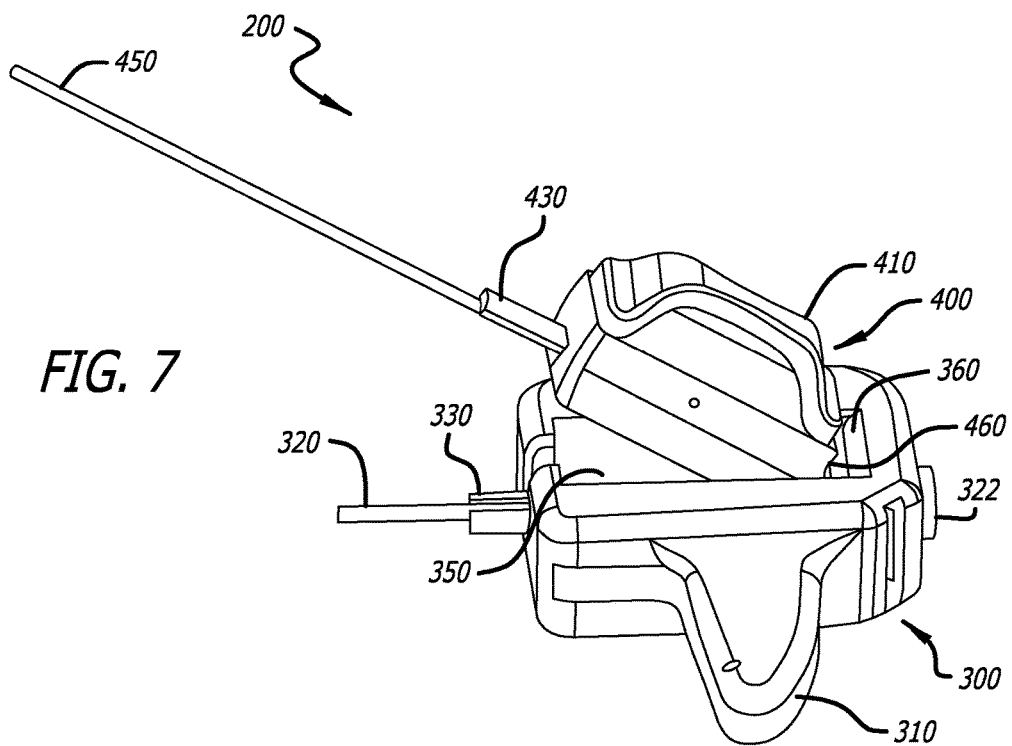
Figure 8:
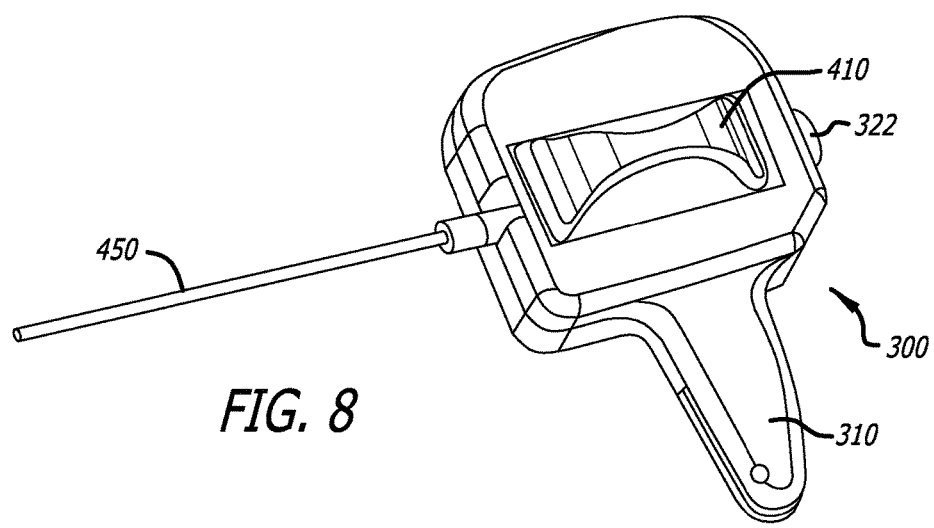

FIG. 6 depicts cartridge assembly 400 being tilted with the end including receiver 460 positioned toward cartridge chamber 350. At such a tilted angle, receiver 460 can interact with guide 360. FIG. 7 depicts the proximal portion of cartridge assembly 400 within cartridge chamber 350 and receiver 460 engaged with guide 360. In certain embodiments, receiver 460 and guide 360 interact to allow receiver 460 to pivot about guide 360. When cartridge assembly 400 is substantially within cartridge chamber 350, such as depicted in FIG. 8, guide 360 interacts with receiver 460 to prevent cartridge assembly 400 from laterally escaping from cartridge chamber 350.

The retainer and guide are depicted as interacting in a rotational fashion such that the retainer allow the cartridge to pivot about the guide and become securely placed within the cartridge chamber. However, other configurations and interactions between a retainer and guide are within the scope of the invention. For example, in certain embodiments the guide is a hinge-like feature that mates with the retainer and the mated retainer/guide assembly rotates together to align the cartridge assembly within the cartridge chamber. In another embodiment, the cartridge can be guided into the chamber with other types of motions, such as a linear motion.

Figure 9:
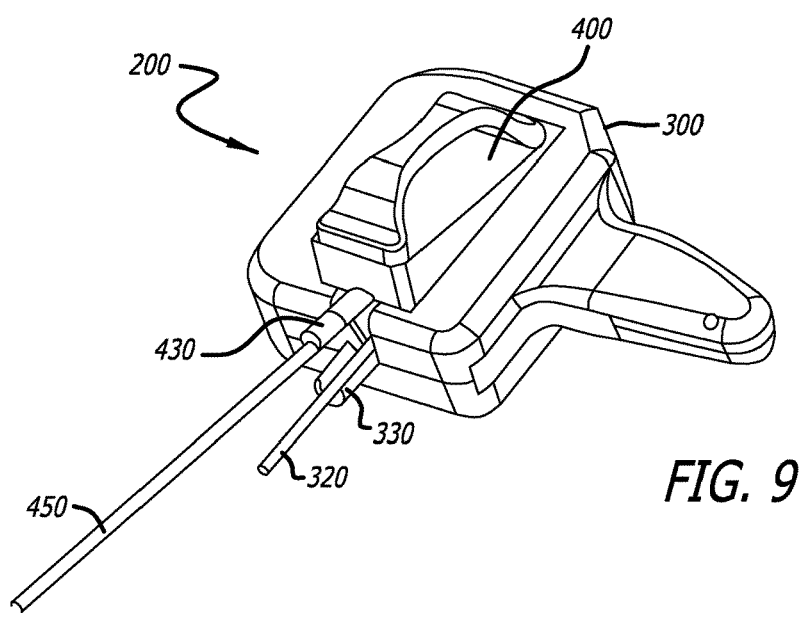
FIG. 9 is a perspective view of an anchor delivery system including a cartridge and a handle showing alignment members on the cartridge and handle.
Figure 10:
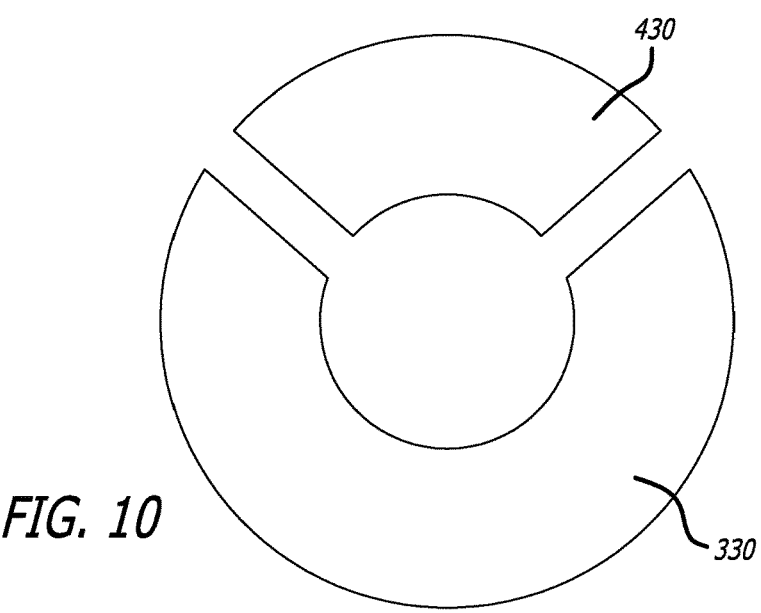
FIG. 10 is a cross-sectional view of the alignment members on the cartridge and handle of an anchor delivery system.

FIG. 9 depicts a view of anchor delivery system 200 in which cartridge assembly 400 has been partially placed within the cartridge chamber of handle assembly 300. FIG. 9 depicts the relationship of cartridge assembly 400 and handle assembly 300 as cartridge assembly is being pivoted into place to assume the configuration of the system depicted in FIG. 8. In this view, the interaction of handle alignment member 330 and cartridge alignment member 430. As depicted in FIG. 10, which is a cross-sectional view, cartridge alignment member 430 mates with handle alignment member 330. In this embodiment, cartridge alignment member 430 has a wedge shape that fits within the wedge recess of handle alignment member 330. In some embodiments, the handle alignment member 330 has a wedge shape that fits within the wedge recess of cartridge alignment member 430. The interaction of the wedge shape and wedge recess provides an aligned orientation of the cartridge and handle.

In certain embodiments, the proximal portion of sheath 28 fits over the union of cartridge alignment member 430 and handle alignment member 330. Each of these members can have a distal taper. For example, FIG. 11 depicts tapered section 431 of cartridge alignment member 430. Such tapered sections on one or both of the alignment members enables the sheath to slide over the union of the alignment members and simultaneously cinch together the wedge and wedge recess of the members. These embodiments take advantage of the presence of the sheath in the urological procedure to secure, or improve the security of, the cartridge and the handle. Further, the sheath can include a locking device. The locking device can interact with the alignment members or it can further secure the alignment members that have been slid within the sheath when the locking device is locked. An alternative embodiment does not utilize a sheath and has a slidably engaging cinching member on the cartridge shaft 450 or handle shaft 320.

FIGS. 11 and 12 depict views of cartridge assembly 400, which includes cartridge shaft 450 extending from a distal portion of the cartridge assembly 400. Cartridge shaft 450 is configured to interact with an endoscope (not pictured) that is coupled to the handle assembly. The proximal portion of cartridge shaft 450 aligns with handle shaft 320 (depicted in FIGS. 5 through 7, for example) via the handle and cartridge alignment members disclosed herein (or their equivalents). The distal portion of cartridge shaft 450 aligns with the distal portion of the endscope. The distal portion of each can interact via a press fitting, a friction fit, or other equivalent mechanism.

Figure 13:
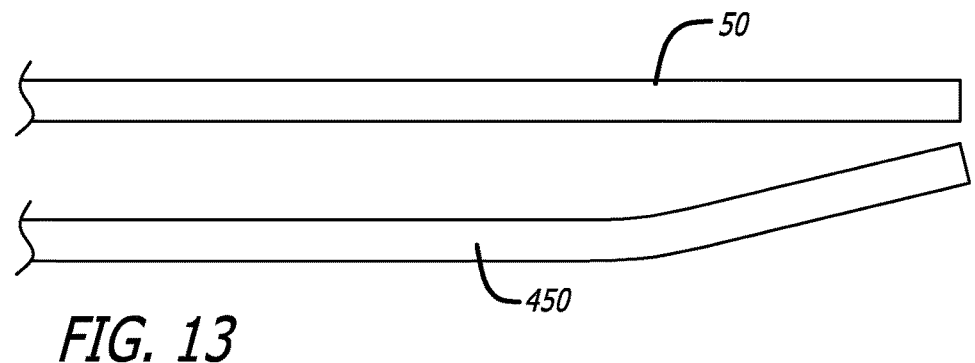
FIG. 13 is a view of the distal portions of a scope and a cartridge shaft.

In certain embodiments, the cartridge shaft 450 is slightly biased toward the position of the endscope such that the distal portion of the cartridge shaft 450 is deflected by a few degrees in the direction of the endoscope. FIG. 13 depicts a distal portion of a scope 50, which is substantially straight, and a distal portion of cartridge shaft 450, which is biased towards the scope. When the distal portions are placed adjacent by pivoting the cartridge assembly in the handle assembly as described herein (or via a similar method of placing the cartridge assembly within the handle assembly), the biased portion of the shaft deflects to substantially align with the longitudinal axis of the scope. Alternatively, the cartridge shaft 450 could engage onto the handle shaft 320 through a close fit or snap fit.

Figure 14:
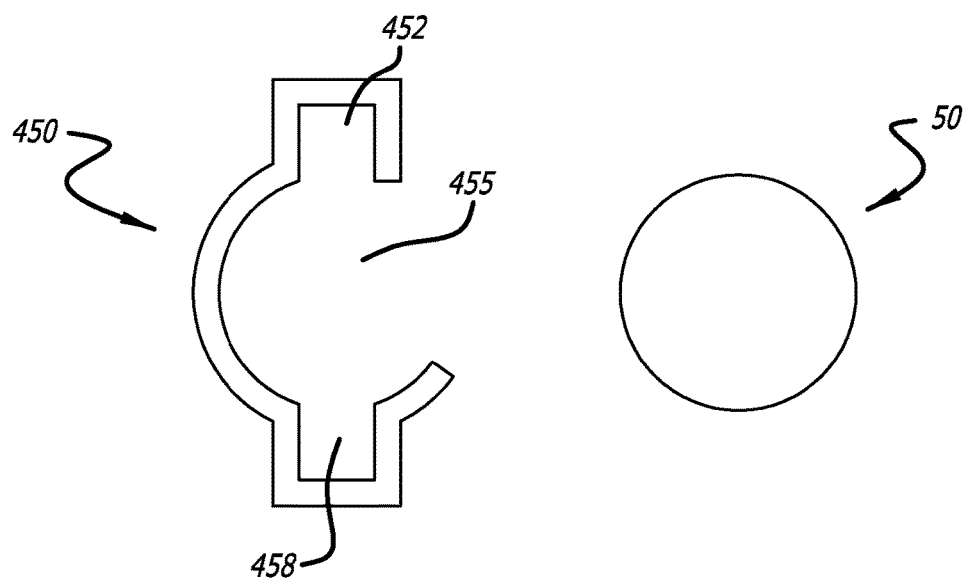
FIG. 14 is a cross-section view of portions of a scope and a cartridge shaft.

The proximal portion of the cartridge shaft can be aligned with the scope via the alignment members and the distal portion of the cartridge shaft can be aligned with the scope via the biasing of that distal portion. FIG. 14 depicts a cross-sectional view of the cartridge shaft 450 and the scope according to one embodiment. The middle portion of the cross-section includes a scope lumen 455. One either side of the scope lumen 455 are upper lumen 452 and lower lumen 458. In this embodiment, when the scope 50 is aligned and fit at least partially within the scope lumen 455, the scope 50 forms an additional wall for both upper lumen 452 and lower lumen 458. The scope lumen 455 is sized and configured to provide a relatively close fit with the scope. Thus, embodiments of the invention provide mechanisms for aligning the proximal, distal, and middle sections of the cartridge shaft with a scope.

While lumens 452 and 458 are described as upper and lower lumens, in use these lumens are not necessarily in an upper and lower orientation. For example, in embodiments where the physician uses the delivery device coupled with the endoscope to depress the urethra into the prostate gland compressing the adenoma and creating the desired opening through the urethra, lumens 452 or 458 are in contact with the prostate gland. The outer surface of these lumens is the surface of the device that is applying pressure to the prostate gland. The delivery device and the endoscope are therefore able to move together without the risk of the scope exiting the open side of cartridge shaft 452 because the direction of pressure is generally orthogonal to that opening.

The upper and lower lumens of the cartridge shaft are used to house and deploy parts of the anchors delivered by the anchor delivery system. The anchor components can be housed in a distal portion of the lumens of the cartridge shaft. A substantial portion of the length of these lumens may contain pusher or puller mechanisms to transmit mechanical forces from the handle to the distal portion of the cartridge shaft to assemble the anchor as described herein.

Figure 15:
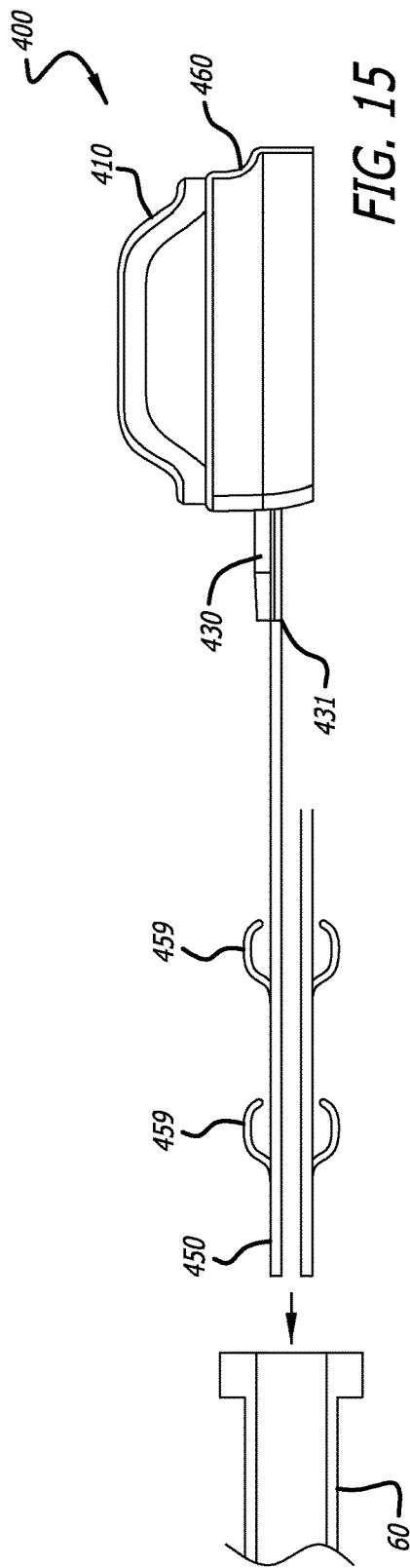
FIG. 15 illustrates a cartridge shaft and handle shaft entering a sheath.
Figure 16:
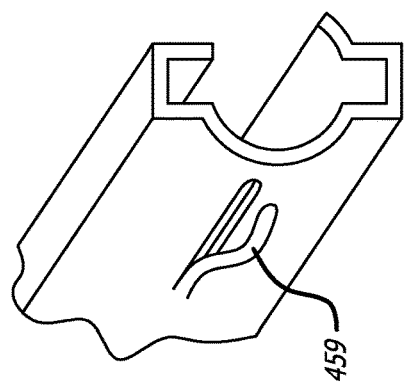
FIG. 16 illustrates and embodiment of a cartridge shaft.

FIGS. 15 and 16 depict features 459 configured to engage the sheath 60. These spring features can be included on the cartridge shaft 450 or the handle shaft 320 to bias one shaft towards the other as the anchor delivery system is advanced into the sheath. Other features, such as bumps, protrusions, ridges, and the like, that enhance the alignment of the cartridge shaft and handle shaft can be included on each.

FIG. 17 depicts a kit including a handle assembly 300 and four cartridge assemblies 400. FIGS. 18A through 18D depict various designs for a cartridge grip 310 to facilitate proper placement of a cartridge within the handle.

Figure 19A:
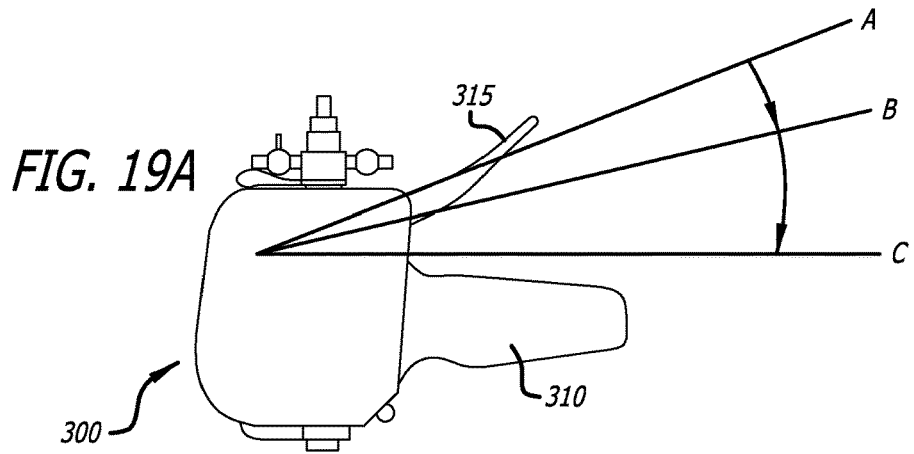
FIGS. 19A through 19C depict an actuation sequence for a handle.
Figure 19B:
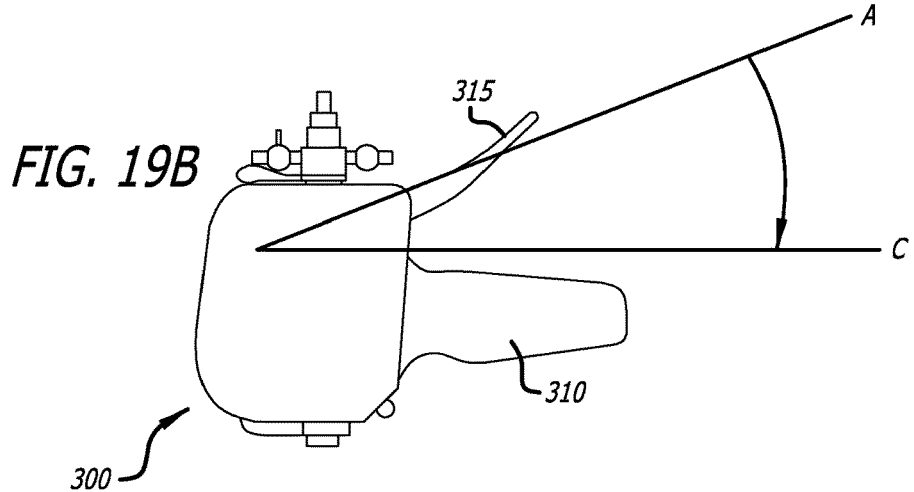
Figure 19C:
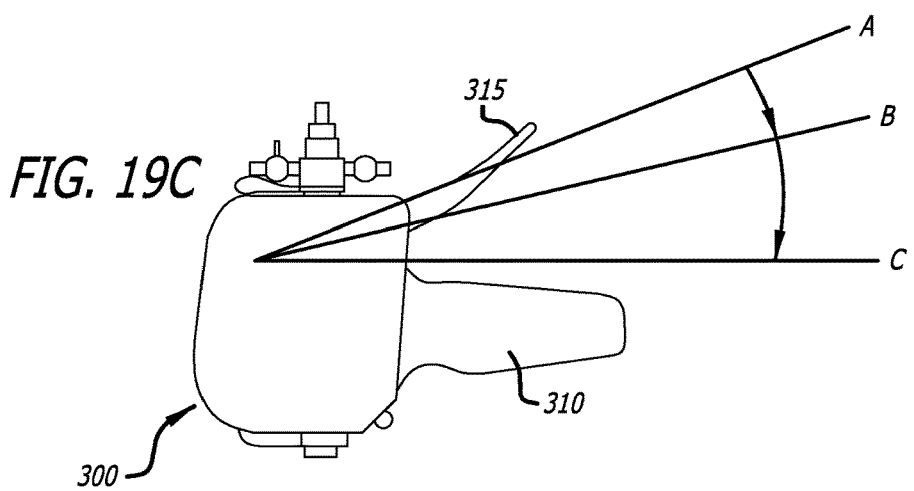

FIGS. 19A through 19C depict an actuation sequence for a handle 300. In FIG. 19A, at position A, the lever 315 is fully extended and the device is ready for operation. When pulled to position B, the needle deploys from the distal portion of the device. At position C, the needle retracts back into the device. In FIG. 19B, the lever 315 has returned to its fully extended position A and is ready for a second squeeze sequence, which further retracts the needle back into the device until position C where the connector attached to the distal anchor is tensioned. In FIG. 19C, the lever 315 has returned to its fully extended position A and is ready for a third squeeze sequence. At position B, the second (or proximal) anchor is attached to the connector, which is cut proximal to this second connection. At position C, energy has been fully restored to the relevant springs and the lever 315 is free to return to position A to begin a new delivery sequence with a new cartridge.

FIGS. 20A through 20D depict various shapes and configurations of a handle 300. The handle 300 can have one lever 315, such as depicted in FIGS. 20B, 20C, and 20D, or the handle can have more than one lever, such as levers 315a and 315b depicted in FIG. 20A. FIGS. 20B, 20C, and 20D depict various embodiments of a handle ridge 302 and handle recess 301. The handle ridge 302 and handle recess 301 cooperate to provide an ergonomic interface to the user's hands with the handle 300. In some instanced, the procedure is best accomplished with subtle movements of the handle and the handle ridge 302 and handle recess 301 can provide secure and comfortable interaction between the handle 300 and the user.

The method of use of the anchor delivery system can incorporate the use of a cystoscope, endoscope, or similar visualization device. In some embodiments, the proximal handle includes a scope lock with no moving parts for locking a cystoscope to the handle prior to performing the treatments disclosed herein. The lack of moving parts reduces the cost and increases the reliability and ease of use.

Embodiments described herein provide several advantages, including, but not limited to, the ability to efficiently deliver multiple anchor assemblies while reducing patient discomfort and increasing ease-of-use. Certain embodiments provide mechanisms for, with a single lever or equivalent actuator, delivering an anchor assembly and recharging the stored energy in the delivery device such that the device is ready or near ready to deliver another anchor assembly by simply replacing a cartridge in the delivery system.

Accordingly, the present invention contemplates both pushing directly on anchor portions of an anchor assembly as well as pushing directly upon the connector of the anchor assembly. Moreover, as presented above, the distal or first anchor component can be advanced and deployed through a needle assembly and at least one component of the proximal or second anchor component is advanced and deployed from the needle or from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the displacement, compression, and/or retraction of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure. In one preferred embodiment, the shape and contour of the anchor assembly is configured so that the assembly invaginates within target tissue, such as within folds formed in the urethra by the opening of the urethra lumen by the anchor assembly. In desired placement, wispy or pillowy tissue in the area collapses around the anchor structure. Eventually, the natural tissue can grow over the anchor assembly and new cell growth occurs over time.

Such cooperation with target tissue facilitates healing and avoids unwanted side effects such as calcification or infection at the interventional site.

Subsequent to the interventional procedure, the patient can be directed to take appropriate drugs or therapeutic agents, such as alpha blockers and anti-inflammatory medicines.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating that retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors that can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism that pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

The invention claimed is:

1. A system for deploying an anchor assembly, comprising:

a handle comprising a cartridge chamber having a back end and an interior surface, wherein the back end comprises an interior protrusion;

a removable cartridge carrying the anchor assembly, the cartridge comprising a receiver, wherein the receiver pivots about the interior protrusion when the cartridge is placed within the cartridge chamber;

a handle alignment feature located in a region of the handle across the cartridge chamber from the interior protrusion;

a cartridge alignment feature located on the cartridge;

an elongate member coupled to the cartridge; and a needle advanceable from a lumen of the elongate member, wherein the anchor assembly is advanced from within the needle.

2. The system of claim 1 wherein the cartridge and handle are configured to couple by first pivoting the cartridge with respect to the handle and then mating the handle alignment feature with the cartridge alignment feature.

3. The system of claim 1 wherein the handle alignment feature has a wedge-shaped cross section.

4. The system of claim 1 wherein the cartridge alignment feature has a wedge-shaped cross section.

5. The system of claim 1 wherein the handle alignment feature comprises a wedge-shaped recess.

6. The system of claim 1 wherein the cartridge alignment feature comprises a wedge-shaped recess.

7. The system of claim 1 further comprising a sheath, wherein the cartridge alignment feature and the handle alignment feature are configured to fit within the sheath.

8. The system of claim 1 wherein the handle further comprises a lever for performing an actuation sequence to deliver the anchor assembly.

9. The system of claim 8 wherein the actuation sequence comprises advancing the needle from the elongate member.

10. The system of claim 9 wherein the actuation sequence further comprises delivering the anchor assembly from the cartridge through the needle.

11. The system of claim 1 wherein the needle advances from an opening located on a side of the elongate member.

12. The system of claim 1 wherein the needle advances from an opening located at a distal end of the elongate member.

* * * * *